United States Patent [19]

Kitame et al.

[11] 4,157,391

[45] Jun. 5, 1979

[54] CHOLESTEROL DERIVATIVE-BASED MEDICAMENTS ACTING ON BIO-PROTECTIVE MECHANISMS

[75] Inventors: Fumio Kitame; Hiroshi Saitoh; Nakao Ishida, all of Sendai, Japan

[73] Assignee: The Green Cross Corporation, Osaka, Japan

[21] Appl. No.: 804,239

[22] Filed: Jun. 7, 1977

[30] Foreign Application Priority Data

Feb. 23, 1977 [JP] Japan .................................. 52/18939

[51] Int. Cl.² ............................................ A61K 31/56
[52] U.S. Cl. ..................................... 424/238; 424/243
[58] Field of Search ....................... 260/397.2; 424/238

[56] References Cited

U.S. PATENT DOCUMENTS 3,974,188  8/1976  Kudo et al. ........................ 260/397.2

OTHER PUBLICATIONS

Chem. Abstracts., vol. 70, (1969), Pars. 47.684m.

Primary Examiner—Elbert L. Roberts
Attorney, Agent, or Firm—Cushman, Darby & Cushman

[57] ABSTRACT

7-Hydroxycholesterol and 7-ketocholesterol can be used as a medicament having a pharmacodynamic action on the bio-protective mechanisms, and thus they are useful as an immunoregulatory agent or antiphlogistic agent.

7 Claims, 1 Drawing Figure

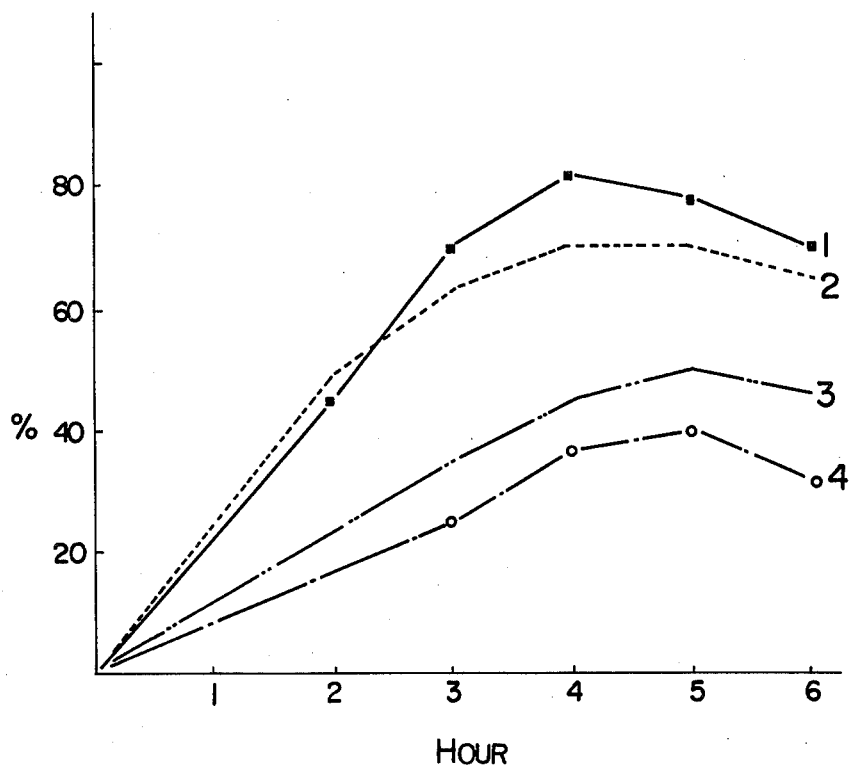

CHOLESTEROL DERIVATIVE-BASED MEDICAMENTS ACTING ON BIO-PROTECTIVE MECHANISMS

This invention relates to medicinal preparations having a pharmacodynamic action on the bio-protective mechanisms in living organisms, said preparations being composed primarily of cholesterol derivatives expressed by the following general formula (I):

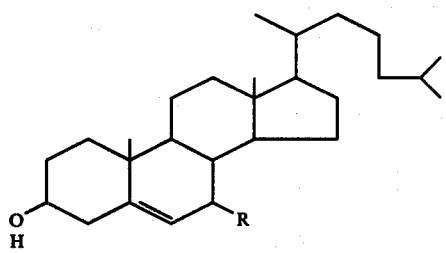

(where R represents —OH or =O).

Among the compounds expressed by the above-shown general formula (I), the most preferred examples for use in this invention are 7-hydroxycholesterol and 7-ketocholesterol.

These compounds are already known in the art and mostly acknowledged as catabolic products of cholesterol in living organisms. This invention is a discovery of novel use of such bio-metabolic products as a medicament. This invention also features finding of the active center of the immunoregulatory substance in living organisms known as IRA.

The present inventors and their co-workers have previously discovered a method for preparation of a peptide-like material having an immunoregulatory activity in serum and placental blood (Japanese Patent Application No. 33421/76). The study on this immunoregulatory substance has been rapid progress even since such substance was isolated from Cohn IV-1 paste of human serum and identified as a peptide-like material with molecular weight of approximately 5,000 by Occhino et al., in 1973 (The Journal of Immunology, 110, (3), 685, (1973)). This peptide-like material is presently called IRA (immunoregulatory α-globulin). The present inventors have also pursued their research into the entity of this immunoregulatory substance acting in the living organisms.

The study by the present inventors has been aimed principally at elucidating the active center of said immunoregulatory substance existing in living organisms and realizing chemical synthesis of the substance which, as compared with the conventional extracts, can be used for a wide variety of remedial purposes such as for immunoregulatory treatment, can be refined to a desired purity and can be also determined both physically and by way of analytical chemistry and which can therefore be administered as a remedial medicament at a correct dosage to the relevant patients.

The present inventors have employed a method in which the slightly water soluble material obtained from Cohn IV-1 paste by organic solvent extraction was subjected to column chromatography to batch off the immunoregulatory active substance, and found out that this substance is a cholesterol derivative. The present inventors also disclosed the fact that this substance has an antiphlogistic activity.

The medicaments of this invention having a pharmacodynamic action on the bio-protective mechanisms are the compounds composed primarily of cholesterol derivatives expressed by the following general formula (I):

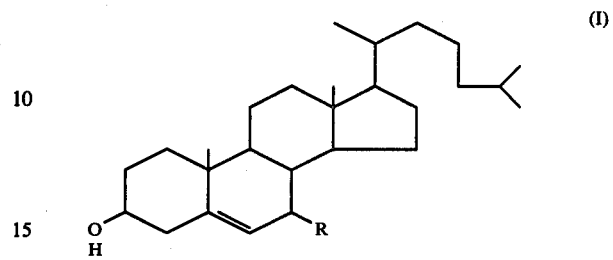

(where R represents —OH or =O).

Typical examples of the compounds expressed by the general formula (I) are 7-hydroxycholesterol and 7-ketocholesterol. For obtaining either of these substances, Cohn IV-1 paste of human serum fraction is extracted with a chloroform-methanol system and the obtained extract is subjected to $Al_2O_3$ and $SiO_2$ column chromatography and further to cellulose and liquid chromatography to batch off the cholesterol derivative fraction. The desired substance is isolated in the form of crystals. They may be also chemically synthesized by merely oxidizing cholesterol according to a known method.

The compounds of the general formula (I) can be used as an immunoregulatory agent, particularly as a cytoplasmic immunoregulatory medicinal base and also prove useful as an antiphlogistic remedial medicament. Now, the general pharmacodynamic activities, method of administration, effective dosage and toxicity of the compounds of the general formula (I) are described.

(1) Immunoregulatory action (in vitro experiments)

The PHA reaction 50% inhibition concentration of the compounds of the general formula (I) were examined by using the PHA method by Cooperband, S. R., et al., (The Journal of Immunology, 109, (1), 154, (1972)). The results are shown in the following table. For sake of comparison, the effect of IRA obtained according to the Occhino et al., method (The Journal of Immunology, 110, (3), 685, (1973)) was also shown.

| | |
|---|---|
| 7-hydroxycholestrol | 5 µg/ml |
| 7-ketocholestrol | 8 µg/ml |
| IRA | 20 µg/ml |

(2) Immunoregulatory action (in vivo experiments)

The following animal tests were conducted by using the compounds of the general formula (I) (7-hydroxycholesterol and 7-ketocholesterol).

Of the total 15 mice used for the tests, 5 mice were given 7-hydroxycholesterol (at the dose of 8 mg/kg/day) and another 5 mice were given 7-ketocholesterol (at the dose of 10 mg/kg/day), both through intravenous administration continuously for 20 days, and the effect on skin grafting was examined. For administration, each compound was emulsified with a surface active agent and prepared into a physiological isotonic solution with end concentration of 3.0 weight %, and this solution was previously administered to each mouse of the above-said two test groups 24 hours before start of grafting, and thereafter the solution was administered once a day for the total period of 20 days.

The surface observation after 20-day test showed that the skin-grafted ratio of 80 to 90% in said both tested groups in contrast with 0% in the control. This is indicative of the excellent pharmacodynamic effect of the compounds of this invention as an immunoregulatory medicament.

(3) Antiphlogistic action

20 Mice were divided into four groups of five and the mice of two test groups were administered intra-abdominally with 7-hydroxycholesterol and 7-ketocholesterol, respectively, with the dose of 200 mg/kg (physiologically isotonic 2.0 weight % aqueous solution), and 1 hour later, 0.05 ml of 1% carrageenin was administered as a phlogogenic agent subcutaneously to the hind legs of these mice.

The sizes of the edemata grown on the mice legs with time after carrageenin administration were measured by a volume differential meter and compared with those of the control mice to which an isotonic sodium chloride solution was administered.

There was observed 82% growth of edema in four hours after carrageenin administration in the mice of the control group and 70% growth of edema in the cholesterol group (this group was administered with cholesterol for reference data). In the 7-hydroxycholesterol group, on the other hand, the growth of edema was limited to about 40% in five hours after carrageenin administration, signifying an excellent antiphlogistic effect of this compound. In the 7-ketocholesterol group, there was seen only about 50% growth of edema, attesting to a notable antiphlogistic action of this compound, too.

In the single FIGURE of the drawings there is disclosed a graph of the percent growth of edema against time after carragenin administration.

The test results are shown in the graph of FIG. 1 of the accompanying drawing. In the graph, percent of growth of edema is given on the vertical Y-axis and time (hour) after carrageenin administration is given on the horizontal X-axis. The numerals for the respective curves represent the respective specimens used in the test, that is, 1 represents isotonic sodium chloride solution, 2 cholesterol, 3 7-ketocholesterol, and 4 7-hydroxycholesterol.

(4) Dosage and method of administration

The 50 percent effective doses of 7-hydroxycholesterol and 7-ketocholesterol for the immunoregulatory and antiphlogistic activities were examined by way of animal experiments. It was ascertained that the most preferred form of administration for remedial use as a medication is injection, and the recommended dosage is 10 to 1,000 mg/kg in gross volume. The compounds are also effective when administered externally or orally, but the dosage in such cases is usually 40 to 2,000 mg/kg in gross volume. In the case of external administration, a small dosage will do as localized application is possible.

For use as an injection, it is recommended to prepare the material of this invention into a physiologically isotonic aqueous solution by emulsifying the material with a suitable emulsifier as the material of this invention is insoluble in water. The emulsifier used for this purpose may be selected from the known types of compounds commonly used for medicinal preparations. The loadings of such emulsifier should be 2 to 10% by weight. The compounds of this invention can be contained in an amount of 1.0 to 60% by weight in the medicament. It is also possible to contain 10 to 1,000 mg of active principle in the composition.

When the compounds of this invention are used in the form of an aqueous solution, it is highly advantageous to add a stabilizer of the known types of steroid such as albumin. Such stabilizer may be added in loadings of 0.1 to 5 weight % for obtaining due effect.

When used for oral administration, the compounds of this invention may be prepared into suitable tablets or liquids according to a pertinent method known in the art. The cholesterol derivatives used in the medicaments according to this invention are scarcely disintegrated in the stomach, and there are even available some data suggestive of absorption from the stomach and intestinal tracts. Thus, it seems that no specific consideration is needed in preparation of the medicaments for oral administration.

The compounds of this invention can be also prepared into an oitment for external use according to a known method. In this case, an immediate effect is obtained as the preparation can be acted directly to the affected part.

(5) Acute toxicity test

An acute toxicity test of 7-hydroxycholesterol and 7-ketocholesterol was conducted on one group of rats (5 rats) with average body weight of about 200 gr. Each compound was suspended in a physiological solution of sodium chloride and made into a uniform suspension by a supersonic treatment, and then such suspension was administered intro-abdominally to each rat at the doses of 500 mg/kg, 1,000 mg/kg, 1,500 mg/kg and 2,000 mg/kg, respectively. No death was seen in 5-day observation of the tested rats.

As understood from the foregoing description, the medicaments acting on the bio-protective mechanisms according to this invention have little toxicity and no antigenic properties as they contain as active principle a substance identical with the active center of IRA which derives itself from the living organisms.

It is to be also noted that the in vitro experiments show an extremely high specific activity of the compounds of this invention as compared with the compounds which have been known heretofore as IRA. Further, as the medicaments of this invention were confirmed as composed of a single compound, it is possible to adjust the dosage to avoid any excess administration. Further, as these compounds can be obtained from a chemical synthesis, their medicinal preparations can be provided at extremely low cost.

Shown in the following are some examples of the method for production of the compounds according to this invention.

Production Example 1

25 Grams of commercially available guaranteed cholesterol (a product by Kishida Chemicals) was dissolved in 1,000 ml of hot ethanol, and the entire amount of the mixture was added portionwise into a solution prepared by dissolving 5 grams of sodium stearate (a product by Kishida Chemicals) in 5 liters of distilled water of about 70° C., with pH of the solution being adjusted to 8.5±0.1.

Then a cooling pipe was connected to the top of the reactor and the external portion of the reaction solution was heated while preventing evaporation of the solution, and when the solution temperature reached 85°±1° C., the reaction solution was subjected to aeration for 5 to 7 hours.

After the reaction, a small quantity of hydrochloric acid was added to make the solution acidic (pH: 6–4) and then, by adding an equivalent quantity of chloroform and agitating the mixture vigorously, the object material was extracted while collecting the chloroform layer. Such extracting operation was repeated twice and the collected chloroform layer was concentrated by heating it to around 45° C. under vacuum. This concentrated extract was then dissolved in a small amount of chloroform and poured into a column of chloroform-equilibrated silica gel (a product by Melc Inc.), whereby the object material was adsorbed in the silica gel.

Washing with chloroform caused elution of first the unreacted cholesterol and then 7-ketocholesterol detected by an ultraviolet light irradiator, and further pouring of a solvent prepared by adding methanol in the ratio of 5% to chloroform resulted in elution of 7-hydroxycholesterol.

The eluted 7-ketocholesterol portion and 7-hydroxycholesterol portion were collected respectively and subjected to a similar treatment with a column of benzene-equilibrated silica gel (product by Melc Inc.) for increasing purity.

The melting points of thus obtained 7-ketocholesterol and 7-hydroxycholesterol agreed with those shown in the literature (The Journal of Biological Chemistry, 141, 597, (1941)). The above-mentioned literature, secondary decomposition products were by-produced due to use of Girard's reagent for separating the two compounds, but in the chromatography method used by the present inventors, it was possible to prevent such secondary reaction.

EXAMPLE 2

1 Kg of paste of IV-1 fraction obtained according to Cohn's alcohol fractionation method was suspended and extracted in 4 liters of CHCl$_3$—MeOH (1:1) mixed solution, and the obtained extract was developed in a silica gel column and the adsorbed material was eluted out with chloroform containing a small amount of methanol. The eluate was concentrated and subjected to cellulose column chromatography and two fractions having the inhibitory activities were removed by means of thin-layer chromatography developed with n-hexane - ethyl acetate (1:1) mixed solution and the PHA method and then concentrated under vacuum to isolate them in the form of crystals. Thin-layer chromatography and elemental analysis confirmed that these materials are 7-ketocholesterol and 7-hydroxycholesterol.

Medicinal Preparation Example 1 (Injection)

300 Grams of sterilized 7-hydroxycholesterol was dissolved in 9 liters of distilled water with 300 grams of a polyoxyethylene-polyoxypropylene copolymer with average molecular weight of 8,350, and the mixture was emulsified and then made isotonic physiologically by adding 1 liter of lactated Ringer's solution to obtain an aqueous solution with final concentration of 3.0% W/V. This solution was distributed into vials such that each vial would contain 100 mg of 7-hydroxycholesterol, thereby preparing injections.

Medicinal Preparation Example 2 (Oral tablets)

The following substances:

| 7-hydroxycholestrol | 300 grams |
|---|---|
| Calcium phosphate | 50 grams |
| Starch | 600 grams |
| Liquid gelatin | 150 grams | were mixed and kneaded by adding water, and the mixture was granulated into globular grains and the latter were dried under vacuum to obtain grains with diameter of about 5 mm. These grains were compressed by a presser and prepared into tablets each weighing 500 mg.

Medicinal Preparation Example 3

10 Grams of a mixture of 7-ketocholesterol and 7-hydroxycholesterol and 10 grams of phospholipid were suspended in 100 ml of water, and the suspension was uniformalized by a supersonic treatment and prepared into aseptic injections.

Medicinal Preparation Example 4

10 Grams of phospholipid was added in 100 grams of soya-bean oil, to which were further added 4 grams of 7-hydroxycholesterol and 400 ml of water, and the mixture was prepared into a uniform and steril injection by using a supersonic treating method.

What is claimed is:

1. A medicament having an immuno regulatory action, which comprises a cholesterol derivative expressed by the following general formula:

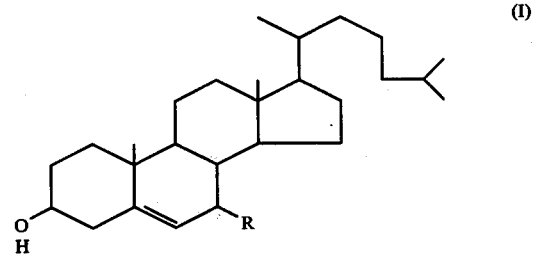

(I)

where R represents —OH or =O, and physiologically acceptable carrier, said medicament containing 10 to 1,000 mg of the cholesterol derivative, the cholesterol derivative being present in an amount of 1.0 to 60% by weight of the medicament.

2. The medicament of claim 1, wherein the cholesterol derivative is 7-hydroxycholesterol.

3. The medicament of claim 1, wherein the cholesterol derivative is 7-ketocholesterol.

4. The medicament of claim 1 in the form of injection.

5. The medicament of claim 1 in the form of orally administrative medicament.

6. A method of imparting to a living organism an immunoregulatory action comprising injecting into the body of the organisms 10 to 1000 mg/kg of a compound of claim 1.

7. A method of imparting to a living organism an immunoregulatory action comprising administering to the organism externally or orally 40 to 2000 mg/kg of the compound of claim 1.